United States Patent
Li-Bovet et al.

Patent Number: 5,849,265
Date of Patent: Dec. 15, 1998

[54] PHARMACEUTICAL AEROSOL FORMULATION COMPRISING A MEDICAMENT, A PROPELLANT AND A FLUORINATED SURFACTANT

[75] Inventors: Li Li-Bovet, Scotch Plains, N.J.; Keith A. Johnson, Chapel Hill, N.C.

[73] Assignee: Glaxo Wellcome Inc., Research Triangle Park, N.C.

[21] Appl. No.: 809,764

[22] PCT Filed: Sep. 27, 1995

[86] PCT No.: PCT/IB95/00866

§ 371 Date: Mar. 27, 1997

§ 102(e) Date: Mar. 27, 1997

[87] PCT Pub. No.: WO96/09816

PCT Pub. Date: Apr. 4, 1996

[30] Foreign Application Priority Data

Sep. 28, 1994 [GB] United Kingdom .................. 9419536

[51] Int. Cl.[6] .............................. A61L 9/04; A61K 31/56; A61K 31/52; A61K 31/35; A61K 31/135
[52] U.S. Cl. ............................. 424/45; 514/180; 514/265; 514/456; 514/653; 514/975
[58] Field of Search ............................. 424/45; 514/180, 514/265, 456, 653, 975

[56] References Cited

U.S. PATENT DOCUMENTS

| | | | |
|---|---|---|---|
| 4,352,789 | 10/1982 | Thiel | 424/46 |
| 5,126,123 | 6/1992 | Johnson | 424/45 |
| 5,344,930 | 9/1994 | Riess et al. | 544/84 |

FOREIGN PATENT DOCUMENTS

| | | | |
|---|---|---|---|
| 0372777 | 6/1990 | European Pat. Off. | A61K 9/12 |
| A 0478686 | 4/1992 | European Pat. Off. | |
| WO A 8604233 | 7/1986 | WIPO | |
| 91/04011 | 4/1991 | WIPO | A61K 9/12 |
| 91/11173 | 8/1991 | WIPO | A61K 9/12 |
| 91/11495 | 8/1991 | WIPO | A61K 9/72 |
| 91/14422 | 10/1991 | WIPO | A61K 9/12 |
| WO A 9200062 | 1/1992 | WIPO | |

*Primary Examiner*—Kimberly Jordan
*Attorney, Agent, or Firm*—James P. Riek

[57] ABSTRACT

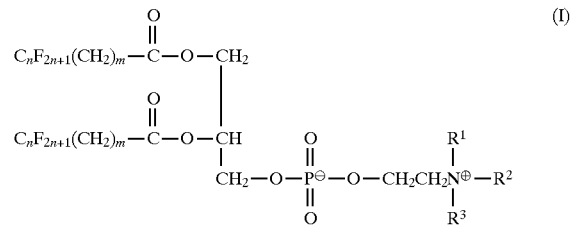

A pharmaceutical aerosol formulation which comprises particulate medicament, a fluorocarbon of hydrogen-containing chlorofluorocarbon propellant and a surfactant of general formula (I), wherein n is an integer of 1 to 18; m is an integer of 0 to 17; and $R^1$, $R^2$ and $R^3$ are each independently a hydrogen atom or a $C_{1-4}$alkyl group.

19 Claims, No Drawings

PHARMACEUTICAL AEROSOL FORMULATION COMPRISING A MEDICAMENT, A PROPELLANT AND A FLUORINATED SURFACTANT

This application is filed pursuant to 35 U.S.C. §371 as a United States National Phase Application of International Application No. PCT/IB95/00866, filed 27 Sep. 1995, which claims priority from 9419536.9 (GB), filed 28 Sep. 1994.

This invention relates to aerosol formulations of use for the administration of medicaments by inhalation.

The use of aerosols to administer medicaments has been known for several decades. Such aerosols generally comprise the medicament, one or more chlorofluorocarbon propellants and either a surfactant or a solvent, such as ethanol. The most commonly used aerosol propellants for medicaments have been propellant 11 ($CCl_3F$) and/or propellant 114 ($CF_2ClCF_2Cl$) with propellant 12 ($CCl_2F_2$). However these propellants are now believed to provoke the degradation of stratospheric ozone and there is thus a need to provide aerosol formulations for medicaments which employ so called "ozone-friendly" propellants.

A class of propellants which are believed to have minimal ozone-depleting effects in comparison to conventional chlorofluorocarbons comprise fluorocarbons and hydrogen-containing chlorofluorocarbons, and a number of medicinal aerosol formulations using such propellant systems are disclosed in, for example, EP 0372777, WO91/04011, WO91/11173, WO91/11495 and WO91/14422. These applications are all concerned with the preparation of pressurised aerosols for the administration of medicaments and seek to overcome the problems associated with the use of the new class of propellants, in particular the problems of stability associated with the pharmaceutical formulations prepared. The applications all propose the addition of one or more of adjuvants such as alcohols, alkanes, dimethyl ether, surfactants (including fluorinated and non-fluorinated surfactants, carboxylic acids, polyethoxylates etc) and even conventional chlorofluorocarbon propellants in small amounts intended to minimise potential ozone damage.

It is well established in the art that fluorinated surfactants may be used to stabilise micronised drug suspensions in hydrofluorocarbon propellants such as 1,1,1,2-tetrafluoroethane (P134a), see for example U.S. Pat. No. 5,126,123, WO91/11173, WO91/14422 and WO92/00062. Surprisingly, the applicants have now found that a particular group of fluorinated surfactants may be used to prepare novel aerosol formulations, and can be advantageous in terms of reducing drug deposition, increasing shelf life and like.

Thus, in one aspect the invention provides a pharmaceutical aerosol formulation which comprises particulate medicament, a fluorocarbon or hydrogen-containing chlorofluorocarbon propellant and a surfactant of general formula (Ia) or (Ib)

$$\begin{array}{c} R^1-CH_2 \\ | \\ (R_2-CH)_r \\ | \\ CH_2-O-P-X \\ | \\ Y \end{array} \quad \text{(Ia)}$$

or $$\begin{array}{c} R^1-CH_2 \\ | \\ CH-O-P-X \\ | \quad | \\ R^2-CH_2 \quad Y \end{array} \quad \text{(Ib)}$$

wherein:

$R^1$ represents:
  $R_F(CH_2)_a-(CH=CH)_b-(CH_2)_c-(CH=CH)_d-(CH_2)_e-A-$;
  $R_F-(CH_2)_f-OCH_2CH(CH_2OH)CH_2-A-$;
  $R_F-(CH_2)_g-OCH_2CH(CH_2OH)-A-$;
  wherein $-A-$ represents $-O-$, $-C(O)O-$, $-R^6(R^7)N^+-$, (wherein each of $R^6$ and $R^7$ represents $C_1-C_4$ alkyl or hydroxyethyl), $-(CH_2)_t-$, wherein t=0 or 1 or $-C(O)N(R^9)-(CH_2)_q-B$, wherein q is an integer from 0 to 12, B represents $-O-$ or $-C(O)-$, and $R^9$ is hydrogen or $R^6$,
  and wherein the sum of a+c+e is from 0 to 17, especially 0 to 11, the sum b+d is from 0 to 12 and each of f and g is from 1 to 12;
  $R_F-(CH_2-CH_2-O)_h-$;
  $R_F-(CH(CH_3)CH_2O)_h-$;
  $R_F-(-CH_2-CH_2-S)_h-$,
  wherein h is from 1 to 12; and
  wherein $R_F$ represents a fluorine-containing moiety having one of the following structures:
  (a) $F(CF_2)_i-$, wherein i is from 1 to 18, especially 2 to 12
  (b) $(CF_3)_2CF(CF_2)_j-$, wherein j is from 0 to 8
  (c) $R_F1(CF_2CF(CF_3))_k-$, wherein k is from 1 to 4, and $R_F1$ represents $CF_3-$, $C_2F_5-$ or $(CF_3)_2CF-$,
  (d) $R_F2(R_F3)CFO(CF_2CF_2)_l$ wherein l is from 1 to 6 and wherein each of $R_F2$ and $R_F3$ independently represents $CF_3-$, $C_2F_5-$, n-$C_3F_7-$ or $CF_3CF_2CF(CF_3)-$ or $R_F2$ and $R_F3$ taken together represent $-(CF_2)_4-$ or $-(CF_2)_5-$, or
  (e) one of the structures (a) to (d) in which one or more of the fluorine atoms are replaced by one or more hydrogen or bromine atoms and/or at least two chlorine atoms in a proportion such that at least 50% of the atoms bonded to the carbon skeleton of $R_F$ are fluorine atoms, and wherein $R_F$ contains at least 4 fluorine atoms, r is 0 or 1;
$R^2$ represents $R^1$, hydrogen or a group OR,
wherein R represents a saturated or unsaturated $C_1-C_{20}$ alkyl or $C_3-C_{20}$ acyl;
and when r is 1, $R^1$ and $R^2$ may exchange their positions; and
each of X and Y independently represent:
  hydroxyl;
  $-OCH_2CH(OH)CH_2OH$;
  $-O(CH_2CH_2O)_tR^3$,
  wherein t is an integer from 1 to 5; and $R^3$ represents a hydrogen atom or $C_1-C_4$ alkyl group;
  $-NR^4R^5$ or $N^+R^4R^5R^8$,
  wherein each of $R^4$, $R^5$ and $R^8$ independently represents a hydrogen atom; a $C_1-C_4$ alkyl group, $-CH_2CH_2O(CH_2CH_2O)_sR^3$, wherein s represents an integer of from 1 to 5, or $R^4$ and $R^5$ when taken together represent $-(CH_2)_q$ wherein q is an integer of from 2 to 5, or with the nitrogen atom $R^4$ and $R_5$ form a morpholino group;
  $-O(CH_2)_pZ$ wherein Z represents a 2-aminoacetic acid group, $-NR^4R^5$ or $-N^+R^4R^5R^8$ where $R^8$ is as defined for $R^4$ and $R^5$ above, and p is an integer of from 1 to 5;

with the proviso that X and Y do not both represent hydroxyl or an ionized form derived from hydroxyl.

The compounds of formula (Ia) and (Ib) are described in EP-0478686, which is incorporated herein by reference, and suitable compounds of formula (Ia) and (Ib) and processes for their preparation may readily be determined by reference thereto. However, the applicants have found that a particular group of compounds of formula (Ia) are especially preferred for use in the formulations of the present invention.

Thus, in a further aspect the invention provides a pharmaceutical aerosol formulation which comprises particulate medicament, a fluorocarbon or hydrogen-containing chlorofluorocarbon propellant and a surfactant of general formula (I)

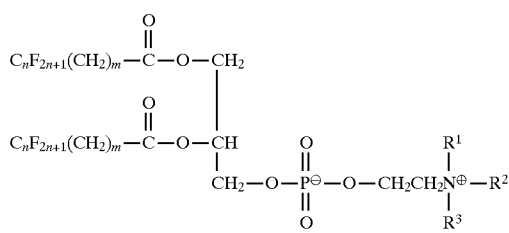

wherein n is an integer of 1 to 18, especially 2 to 12;

m is an integer of 0 to 17, especially 0 to 11; and $R^1$, $R^2$ and $R^3$ are each independently a hydrogen atom or a $C_{1-4}$alkyl group.

Particularly preferred compounds of formula (I) are the fluorinated phosphatidylcholines wherein $R^1$, $R^2$ and $R^3$ each represent methyl, n is an integer of 4 to 8, especially 4 or 6, and m is an integer of 4 to 10, especially 4, 6 or 10.

Certain compounds of formula (I) may contain one or more chiral centres. It will be understood that compounds of formula (I) include all optical isomers of the compounds of formula (I) and mixtures thereof, including racemic mixtures thereof.

Contrary to the teaching in the art, the surfactants employed for the preparation of formulations according to the present invention are effective stabilisers at low concentrations relative to the amount of medicament. Thus, the amount of surfactant employed is desirably in the range of 0.005 to 20% w/w, particularly 0.05 to 20% w/w, more particularly 0.05 to 15% w/w, even more particularly about 0.1 to about 10% w/w, and preferably 0.5 to about 10% w/w, relative to the medicament.

The particle size of the particulate (e.g. micronised) medicament should be such as to permit inhalation of substantially all of the medicament into the lungs upon administration of the aerosol formulation and will thus be less than 100 microns, desirably less than 20 microns, and preferably in the range 1–10 microns, e.g. 1–5 microns.

The final aerosol formulation desirably contains 0.005–10% w/w, preferably 0.005–5% w/w, especially 0.01–1.0% w/w, of medicament relative to the total weight of the formulation.

Medicaments which may be administered in aerosol formulations according to the invention include any drug useful in inhalation therapy and which may be presented in a form which is substantially completely insoluble in the selected propellant. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate, ketotifen or nedocromil; antiinfectives e.g. cephalosporins, penicillins, streptomycin, sulphonamides, tetracyclines and pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutaline, isoetharine, tulobuterol, orciprenaline, or (–)-4-amino-3,5-dichloro-α-[[[6-[2-(2-pyridinyl)ethoxy]hexyl]amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament and/or to minimise the solubility of the medicament in the propellant.

Particularly preferred medicaments for administration using aerosol formulations in accordance with the invention include antiallergics, bronchodilators and antiinflammatory steroids of use in the treatment of respiratory disorders such as asthma by inhalation therapy, for example cromoglycate (e.g. as the sodium salt), salbutamol (e.g. as the free base or the sulphate salt), salmeterol (e.g. as the xinafoate salt), terbutaline (e.g. as the sulphate salt), reproterol (e.g. as the hydrochloride salt), a beclomethasone ester (e.g. the diproprionate), a fluticasone ester (e.g. the propionate) or (–)-4-amino-3,5-dichloro-α-[[[6-[2-(2 -pyridinyl)ethoxy] hexyl]amino]methyl]benzenemethanol. Salmeterol, especially salmeterol xinafoate, salbutamol, fluticasone propionate, beclomethasone dipropionate and physiologically acceptable salts and solvates thereof are especially preferred.

It will be appreciated by those skilled in the art that the aerosol formulations according to the invention may, if desired, contain a combination of two or more active ingredients. Aerosol compositions containing two active ingredients (in a conventional propellant system) are known, for example, for the treatment of respiratory disorders such as asthma. Accordingly the present invention further provides aerosol formulations in accordance with the invention which contain two or more particulate medicaments. Thus suitable combinations of bronchodilatory agents include ephedrine and theophylline, fenoterol and ipratropium, and isoetharine and phenylephrine aerosol formulations.

Preferred aerosol formulations in accordance with the invention comprise (a) an effective amount of a particulate bronchodilatory medicament, (b) an effective amount of a particulate antiinflammatory, preferably a steroidal antiinflammatory medicament, (c) a fluorocarbon or hydrogen-containing chlorofluorocarbon propellant, and (d) a surfactant of general formula (1). Particularly preferred aerosol formulations contain bronchodilators such as salbutamol (e.g. as the free base or as the sulphate salt), salmeterol (e.g. as the xinafoate salt) or isoprenaline in combination with an antiinflammatory steroid such as a beclomethasone ester (e.g. the diproprionate) or a fluticasone ester (e.g. the propionate). Alternatively aerosol formulations may contain a bronchodilator in combination with an antiallergic such as cromoglycate (e.g. the sodium salt). Combinations of isoprenaline and sodium cromoglycate, salmeterol and fluticasone propionate, or salbutamol and beclomethasone dipropionate are especially preferred.

The propellants for use in the invention may be any fluorocarbon or hydrogen-containing chlorofluorocarbon or mixtures thereof having a sufficient vapour pressure to render them effective as propellants. Preferably the propellant will be a non-solvent for the medicament. Suitable propellants include, for example, $C_{1-4}$ hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF_2CH_3$; $C_{1-4}$-hydrogen-containing fluorocarbons such as $CHF_2CHF_2$, $CF_3CH_2F$, $CHF_2CH_3$ and $CF_3CHFCF_3$; and perfluorocarbons such as $CF_3CF_3$ and $CF_3CF_2CF_3$.

Where mixtures of the fluorocarbons or hydrogen-containing chlorofluorocarbons are employed they may be mixtures of the above identified compounds or mixtures, preferably binary mixtures, with other fluorocarbons or hydrogen-containing chloro- fluorocarbons for example $CHClF_2$, $CH_2F_2$ and $CF_3CH_3$. Preferably a single fluorocarbon or hydrogen-containing chlorofluorocarbon is employed as the propellant. Particularly preferred as propellants are $C_{1-4}$ hydrogen-containing fluorocarbons such as 1,1,1,2-tetrafluoroethane ($CF_3CH_2F$) and 1,1,1,2,3,3,3-heptafluoro-n-propane ($CF_3CHFCF_3$).

It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$.

The propellant may additionally contain a volatile adjuvant such as a saturated hydrocarbon for example propane, n-butane, isobutane, pentane and isopentane or a dialkyl ether for example dimethyl ether. In general, up to 50% w/w of the propellant may comprise a volatile hydrocarbon, for example 1 to 30% w/w. However, formulations which are substantially free of volatile adjuvants are preferred. In certain cases, it may be desirable to include appropriate amounts of water, which can be advantageous in modifying the dielectric properties of the propellant.

Polar cosolvents which may be incorporated into the formulations according to the present invention include (.e.g $C_{2-6}$)aliphatic alcohols and polyols such as ethanol, isopropanol and propylene glycol and mixtures thereof. Preferably ethanol will be employed. In general only small quantities (e.g. 0.05 to 3.0% w/w) of polar cosolvent are required to improve the dispersion and the use of quantities in excess of 5% w/w may disadvantageously tend to dissolve the medicament. Formulations preferably contain less than 1% w/w, e.g. about 0.1% w/w of polar cosolvent. Polarity may be determined for example, by the method described in European Patent Application Publication No. 0327777.

In addition to the surfactants of general formula (I), the formulations according to the present invention may optionally contain one or more further ingredients conventionally used in the art of pharmaceutical aerosol formulation. Such optional ingredients include, but are not limited to, one or more conventional surfactants as hereinafter described and which are physiologically acceptable by inhalation, taste masking agents, one or more sugars, buffers, antioxidants, water and chemical stabilisers.

Examples of conventional physiologically acceptable surfactants include oleic acid, sorbitan trioleate (Span $^R$ 85), sorbitan mono-oleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil and sunflower seed oil. Preferred surfactants are lecithin, oleic acid and sorbitan trioleate, for inclusion in a pharmaceutical formulation according to the present invention.

Aptly, the aerosol formulations according to the present invention may contain 0.0001 to 50% w/w, preferably 0.001 to 20, for example 0.001 to 1% of sugar relative to the total weight of the formulation. Generally the ratio of medicament: sugar falls within the range of 1:0.01 to 1:100 preferably 1:0.1 to 1:10. Typical sugars which may be used in the formulations include, for example, sucrose, lactose and dextrose, preferably lactose, and reducing sugars such as mannitol and sorbitol, and may be in micronised or milled form.

A particularly preferred embodiment of the invention provides a pharmaceutical aerosol formulation consisting essentially of one or more particulate medicament, one or more fluorocarbon or hydrogen-containing chlorofluorocarbon propellant and a surfactant of formula (I).

Surfactants according to the present invention can be prepared by techniques well known in the art, as can be seen for example, by reference to EP-0478686 substantially as hereinbefore described. A suitable process for preparing surfactants of compounds of formula (I)

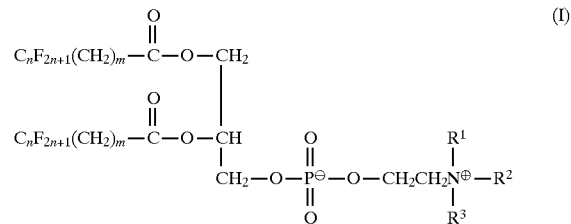

comprises reacting a compound of formula (II)

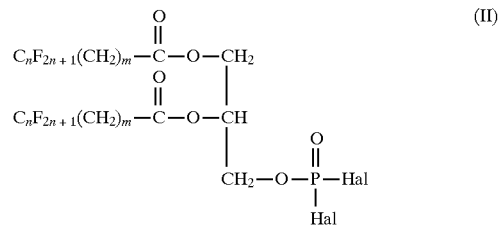

wherein Hal represents a halogen atom selected from fluorine, chlorine, bromine and iodine, with (i) a compound of formula (III)

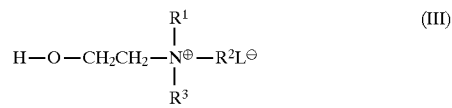

where L is a negatively charged counter ion, such as a halide or an alkyl or arylsulphonyloxy group, such as mesylate or tosylate, and (ii) a hydroxylating agent, such as water.

Suitably the reaction may be carried out in the presence of a chlorinated organic solvent, such as chloroform or the like, and a basic medium, e.g. pyridine or the like.

Compounds of formulae (II) and (III) are well known in the art, and as described above, EP-0478686 is a suitable prior art document which can be referred to.

The formulations of the invention may be prepared by dispersal of the medicament and surfactant in the selected propellant in an appropriate container, e.g. with the aid of sonication. The process is desirably carried out under anhydrous conditions to obviate any adverse effects of moisture on suspension stability.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The suspension stability of the aerosol formulations according to the invention is particularly impressive and may be measured by conventional techniques, for example by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204–207, Appendix XVII C. Such techniques enable the "respirable fraction" of the aerosol formulations to be calculated. As used herein reference to "respirable fraction" means the amount of active ingredient collected in the lower impingement chamber per actuation expressed as a percentage of the total amount of active ingredient delivered per actuation using the twin impinger method described above. The formulations according to the invention have been found to have a respirable fraction of 20% or more by weight of the medicament, preferably 25 to 70%, for example 30 to 60%.

The formulations according to the invention may be filled into canisters suitable for delivering pharmaceutical aerosol formulations. Canisters generally comprise a container capable of withstanding the vapour pressure of the propellant used such as a plastic or plastic-coated glass bottle or preferably a metal can, for example an aluminium can which may optionally be anodised, lacquer-coated and/or plastic-coated, which container is closed with a metering valve. The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The particulate medicament is added to a charge vessel and liquified propellant is pressure filled through the charge vessel into a manufacturing vessel, together with liquified propellant containing the surfactant. The drug suspension is mixed before recirculation to a filling machine and an aliquot of the drug suspension is then filled through the metering valve into the canister. Typically, in batches prepared for pharmaceutical use, each filled canister is check-weighed, coded with a batch number and packed into a tray for storage before release testing.

Each filled canister is conveniently fitted into a suitable channelling device prior to use to form a metered dose inhaler for administration of the medicament into the lungs or nasal cavity of a patient. Suitable channelling devices comprise for example a valve actuator and a cylindrical or cone-like passage through which medicament may be delivered from the filled canister via the metering valve to the nose or mouth of a patient e.g. a mouthpiece actuator. Metered dose inhalers are designed to deliver a fixed unit dosage of medicament per actuation or "puff", for example in the range of 10 to 5000 microgram medicament per puff.

Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1,2,3 or 4 puffs each time.

Suitable daily doses, may be, for example in the range 50 to 200 microgram of salmeterol, 100 to 1000 microgram of salbutamol, 50 to 2000 microgram of fluticasone propionate or 100 to 2000 microgram of beclomethasone dipropionate, depending on the severity of the disease.

Thus, for example, each valve actuation may deliver 25 microgram salmeterol, 100 microgram salbutamol, 25, 50, 125 or 250 microgram fluticasone propionate or 50, 100, 200 or 250 microgram beclomethasone dipropionate. Typically each filled canister for use in a metered dose inhaler contains 100, 160 or 240 metered doses or puffs of medicament.

The filled canisters and metered dose inhalers described herein comprise further aspects of the present invention.

A still further aspect of the present invention comprises a method of treating respiratory disorders such as, for example, asthma, which comprises administration by inhalation of an effective amount of a formulation as herein described.

The following non-limitative Examples serve to illustrate the invention.

EXAMPLE 1

Example 1a

A compound of formula (I) ($R^1$, $R^2$, $R^3$=$CH_3$, n=6, m=6)

To a dry 1 L four neck round bottom flask fitted with mechanical stirring, a temperature probe and nitrogen inlet, was added 150 mL (5 volumes) of dry isopropyl ether (stabilised with BHT). The solution was cooled to −25° C. and then 3.08 mL (5.07 g, 33.07 mmol) of $POCl_3$ was added, followed by 5.53 mL (4.02 g, 39.68 mmol) of triethylamine. The hazy solution was stirred for 5 minutes before the addition of 30.00 g (31.50 mmol) of 8,8,9,9,10,10,11,11,12,12,13,13,13-tridecafluoro-tridecanoic acid 3-hydroxy-2-(8,8,9,9,10,10,11,11,12,12,13,13,13-tridecafluorotridecanoyloxy)-propylester[1] in 75 mL (2.5 vol) of isopropyl ether over a 20 minute time period, being sure to keep the internal temperature between −26° and −23° C.

The mixture was allowed to warm up to 20° C. over the course of 1 hour, and washed with 2×40 mL (2.5 vol) of isopropyl ether, and then the filtrate was evaporated to a volume of about 100 mL at 25° C. CHCl$_3$ (ethanol free 500 mL) was added and the solution was evaporated at 25° C. to a volume of about 100 mL.

[1]. Prepared according to EP-0478686.

120 mL (8.3 vol) of ethanol free chloroform was added. The solution was cooled to 0° C. and then 12.8 mL (12.3 g, 155.6 mmol) of pyridine and 9.56 g (34.7 mmol) of choline tosylate were added. The reaction mixture was allowed to warm up to 25° C. over the course of 1 hour and then stirred for 7 hours at ambient temperature. Water 2.8 mL (155.6 mmol) was added and the mixture was stirred at 25° C. for 5 hours. The mixture was stored overnight at 0° C., and then 250 mL of absolute ethanol was added.

TMD-8 ion exchange resin (400 g) was placed in a 600 mL filter funnel. The resin was washed with absolute ethanol (3×250 mL). The procedure yielded about 300 g of resin after pulling a vacuum for an additional 15 minutes. The TMD-8 ion exchange resin (300 g) was added and the suspension was stirred for 2 hours at 25° C. The resin was filtered, and the cake was washed with 3×250 mL of absolute ethanol. The filtrate was stored overnight at 0° C., and then the solvent was evaporated at a temperature of 25°–30° C. to a total volume of 200 mL. 500 mL toluene was added, and the solvent was evaporated at 50° C. to a volume of about 400 mL at which time the product began to gel out of solution. 500 mL toluene was added and the solvent was evaporated to a total volume of 500 mL. The suspension was stirred vigorously for 12 hours at ambient temperature and the solid powder was collected by filtration. The cake was washed with 2×200 mL of toluene to afford 23.0 g (65.4%) of the title compound.

Example 1b

A compound of formula (I) ($R^1$, $R^2$, $R^3$=CH$_3$, n=4, m=10)

To a dry 2 L four neck round bottom flask fitted with mechanical stirring, temperature probe, nitrogen inlet and septum, was added 100 ml diethylether. The solution was cooled to −20° C., and then 6.7 mL of POCl$_3$ was added, followed by 12.1 mL of triethylamine. 62.5 gm of 12,12,13,13,14,14,15,15,15-Nonafluoropentadecanoic acid 1-hydroxymethyl-2-(12,12,13,13,14,14,15,15,15-nonafluoropentadecanoyloxy)-ethyl ester[1] was dissolved in 500 mL diethylether, chilled in an ice bath, and then added over a 30 minute time period to the POCl$_3$ solution. The mixture was allowed to warm to room temperature.

[1]. Prepared according to EP-0478686.

The mixture was filtered, and washed with 3×100 mL diethylether, and the solvent removed under high vacuum. 100 mL chloroform was added to dissolve the residue, followed by 200 mL acetonitrile, 29.2 mL pyridine and 10.1 gm of choline chloride. The mixture was allowed to warm to room temperature, and then stirred under a nitrogen atmosphere overnight. 6.5 mL of water was then added, and the reaction was stirred at room temperature over 2½ hours.

The solvent was removed on rotary evaporation, and the resulting oil pumped under high vacuum for approximately 1 hour.

Meanwhile, 850 g of ion exchange resin (TMD-8) was treated with 2×1 L chloroform/methanol (4:1) mixture, 2×1 L methanol and 1×1 L chloroform/methanol (4:1).

The compound was diluted in 1,500 mL chloroform, and the ion exchange resin was added, followed by stirring at room temperature for 2 hours. The solvent was then removed, the resultant filtrate rotary evaporated to an oil, and placed in the freezer overnight, and further purified to yield 27.58 gm of the title compound.

Other surfactants of formula (I) described in the Examples hereinafter were prepared by analogous methods.

EXAMPLE 2

Micronised salbutamol base (26 mg) and compound of formula (I) ($R^1$,$R^2$,$R^3$=CH$_3$, n=4, m=10) (5.1 mg) were weighed into a 15 ml transparent glass aerosol vial and a metering valve was crimped into place. 1,1,1,2-Tetrafluoroethane (P134a, 18.2 g) and heptafluoropropane (P227, 21 g) were added to the vial through the valve. The vial was sonicated for 30 sec. to disperse the drug and surfactant.

EXAMPLES 3–6

Using the procedure described in Example 2 the following formulations were prepared:

| Example | Drug | Propellant | Surfactant/mg |
|---|---|---|---|
| 3 | Salbutamol base (26mg) | P227 | 1.2 |
| 4 | Salbutamol base (26mg) | P227 | 11 |
| 5 | Salbutamol sulphate (32mg) | P227 | 3.1 |
| 6 | Salbutamol sulphate (32mg) | P134a | 0.5 |

EXAMPLES 7 to 20

The aerosol formulations of Examples 7 to 20 were prepared in large scale batches. A metering valve (e.g. DF60 valve) was crimped into an 8 ml aluminium can (12.5 ml can in the case of Examples 19 and 20) and the can was purged with 1,1,1,2-tetrafluoroethane prior to filling. The particulate medicament (micronised) was added to a charge vessel and liquified 1,1,1,2-tetrafluoroethane propellant was pressure filled through the charge vessel into a manufacturing vessel, together with liquified propellant containing the surfactant of formula (I) ($R^1$, $R^2$ and $R^3$=CH$_3$, n and m as indicated). The drug suspension was mixed before recirculation to a filling machine and an aliquot (typically 12 g) of the drug suspension was then filled through the metering valve into the canister to provide an inhaler typically containing an equivalent of 160 actuations of 75 mg (designed to deliver 120 actuations). The following inhalers were prepared:

| Example 7 | Per 75.0mg actuation | Per 160 actuations (i.e. per can) |
|---|---|---|
| Fluticasone propionate | 275µg | 44mg |
| Surfactant (n = 4, m = 4) | 27.5µg | 4.4mg |
| 1,1,2-Tetrafluoroethane | to 75.0mg | to 12.0g |

| Example 8 | Per 75.0mg actuation | Per 160 actuations (i.e. per can) |
|---|---|---|
| Fluticasone propionate | 275µg | 44mg |
| Surfactant (n = 4, m = 4) | 2.75µg | 0.44mg |
| 1,1,1,2-Tetrafluoroethane | to 75.0mg | to 12.0g |

| Example 9 | Per 75.0mg actuation | Per 160 actuations (i.e. per can) |
|---|---|---|
| Fluticasone propionate | 275µg | 44mg |
| Surfactant (n = 6, m = 6) | 27.5µg | 4.4mg |
| 1,1,1,2-Tetrafluoroethane | to 75.0mg | to 12.0g |

| Example 10 | Per 75.0mg actuation | Per 160 actuations (i.e. per can) |
|---|---|---|
| Fluticasone propionate | 275µg | 44mg |
| Surfactant (n = 6, m = 6) | 2.75µg | 0.44mg |
| 1,1,1,2-Tetrafluoroethane | to 75.0mg | to 12.0g |

| Example 11 | Per 75.0mg actuation | Per 160 actuations (i.e. per can) |
|---|---|---|
| Fluticasone propionate | 27.5µg | 4.4mg |
| Surfactant (n = 4, m = 4) | 2.75µg | 0.44mg |
| 1,1,1,2-Tetrafluoroethane | to 75.0mg | to 12.0g |

| Example 12 | Per 75.0mg actuation | Per 160 actuations (i.e. per can) |
|---|---|---|
| Fluticasone propionate | 27.5µg | 44mg |
| Surfactant (n = 4, m = 4) | 0.275µg | 0.044mg |
| 1,1,1,2-Tetrafluoroethane | to 75.0mg | to 12.0g |

| Example 13 | Per 75.0mg actuation | Per 160 actuations (i.e. per can) |
|---|---|---|
| Fluticasone propionate | 27.5µg | 4.4mg |
| Surfactant (n = 6, m = 6) | 2.75µg | 0.44mg |
| 1,1,1,2-Tetrafluoroethane | to 75.0mg | to 12.0g |

| Example 14 | Per 75.0mg actuation | Per 160 actuations (i.e. per can) |
|---|---|---|
| Fluticasone propionate | 27.5µg | 4.4mg |
| Surfactant (n = 6, m = 6) | 0.275µg | 0.044mg |
| 1,1,1,2-Tetrafluoroethane | to 75.0mg | to 12.0g |

| Example 15 | Per 75.0mg actuation | Per 160 actuations (i.e. per can) |
|---|---|---|
| Salmeterol xinafoate | 39.88µg | 6.38mg |
| Surfactant (n = 4, m = 4) | 3.99µg | 0.64mg |
| 1,1,1,2-Tetrafluoroethane | to 75.0mg | to 12.0g |

| Example 16 | Per 75.0mg actuation | Per 160 actuations (i.e. per can) |
|---|---|---|
| Salmeterol xinafoate | 39.88µg | 6.38mg |
| Surfactant (n = 4, m = 4) | 0.399µg | 0.064mg |
| 1,1,1,2-Tetrafluoroethane | to 75.0mg | to 12.0g |

| Example 17 | Per 75.0mg actuation | Per 160 actuations (i.e. per can) |
|---|---|---|
| Salmeterol xinafoate | 39.88µg | 6.38mg |
| Surfactant (n = 6, m = 6) | 3.99µg | 0.64mg |
| 1,1,1,2-Tetrafluoroethane | to 75.0mg | to 12.0g |

| Example 18 | Per 75.0mg actuation | Per 160 actuations (i.e. per can) |
|---|---|---|
| Salmeterol xinafoate | 39.88µg | 6.38mg |
| Surfactant (n = 6, m = 6) | 0.399µg | 0.064mg |
| 1,1,1,2-Tetrafluoroethane | to 75.0mg | to 12.0g |

| Example 19 | Per 75.0mg actuation | Per 248 actuations (i.e. per can) |
|---|---|---|
| Beclomethasone dipropionate hydrate | 54.32µg | 13.47mg |
| Surfactant (n = 6, m = 6) | 5.4µg | 1.35mg |
| Purified water B.P. | 0.045mg | 11.16mg |
| 1,1,1,2-Tetrafluoroethane | to 75.0mg | to 18.6g |

Inhaler contains equivalent of 248 actuations (delivers 200 actuations).

| Example 20 | Per 75.0mg actuation | Per 248 actuations (i.e. per can) |
|---|---|---|
| Beclomethasone dipropionate hydrate | 54.32µg | 13.47mg |
| Surfactant (n = 4, m = 4) | 5.4µg | 1.35mg |
| Purified water B.P. | 0.045mg | 11.16mg |
| 1,1,1,2-Tetrafluoroethane | to 75.0mg | to 18.6g |

Inhaler contains equivalent of 248 actuations (delivers 200 actuations).

EXAMPLES 21 to 31

Micronized drug and surfactant were weighed into 15 ml transparent aerosol vials (Wheaton Industries, NJ). A metering valve (Bespak valve No. BK300, or Valois DF60 MK VI) was crimped onto each vial. Finally, 1,1,1,2-tetrafluoroethane (P134a) or 1,1,1,2,3,3,3-heptafluoro-n-propane (P227) was added to the vial through the valve. Vials were then sonicated for 30 seconds.

| Example | Drug (amount) | Surfactant type | Surfactant mg/inhaler | Propellant P134a (18g) or P227 (22g) |
|---|---|---|---|---|
| 21 | Salbutamol Base (26mg) | n = 8, m = 4 | 2.0 | P134a |
| 22 | Salbutamol Base (26mg) | n = 6, m = 10 | 1.8 | P134a |
| 23 | Salbutamol Sulphate (29mg) | n = 6, m = 10 | 2.3 | P134a |
| 24 | Salbutamol Base (26mg) | n = 4, m = 10 | 1.2 | P227 |
| 25 | Salbutamol Base (26mg) | n = 8, m = 4 | 2.0 | P227 |
| 26 | Salbutamol Base (26mg) | n = 6, m = 10 | 2.8 | P227 |
| 27 | Salbutamol Sulphate (26mg) | n = 8, m = 4 | 2.0 | P227 |

| Example | Drug (amount) | Surfactant type | Surfactant mg/inhaler | Propellant P134a (18g) or P227 (22g) |
|---|---|---|---|---|
| 28 | Salbutamol Sulphate (26mg) | n = 6, m = 10 | 2.0 | P227 |
| 29 | Salbutamol Sulphate (26mg) | n = 4, m = 10 | 3.1 | P227 |
| 30 | Salmeterol (9mg) | n = 8, m = 4 | 2.5 | P227 |
| 31 | Salmeterol (9mg) | n = 6, m = 10 | 3.0 | P227 |

EXAMPLES 32 to 43

Stock solutions of surfactants with concentration of 0.33 mg/g were prepared in glass according to the following procedure. 6 mg of surfactant were weighed into the safety coated glass vials. A DF60 MKIV valve was crimped onto the vial using a Pamasol crimper. 18.2 grams of 1,1,1,2-tetrafluoroethane (P134a) were filled through the valve using a Pamasol pressure filler. Then, the inhalers were sonicated for 30 sec to disperse surfactants.

Appropriate amount surfactant or surfactant stock solution was delivered into the safety coated glass vials before a drug was added into these vials. A DF60 MKIV valve was crimped onto the canister, and P134a propellant as received was filled through the valve. After filling was complete, the inhalers were sonicated for 30 sec to disperse the drug and surfactant.

| Example | Drug (amount) | Surfactant type | Surfactant mg/inhaler |
|---|---|---|---|
| 32 | Salbutamol Sulphate (29 mg) | n = 4, m = 10 | 1.0 |
| 33 | Salbutamol Sulphate (29 mg) | n = 4, m = 4 | 1.0 |
| 34 | Salbutamol Sulphate (29 mg) | n = 6, m = 6 | 1.0 |
| 35 | Salbutamol Sulphate (29 mg) | n = 8, m = 4 | 1.0 |
| 36 | Salmeterol (8 mg) | n = 4, m = 10 | 0.1 |
| 37 | Salmeterol (8 mg) | n = 4, m = 4 | 0.1 |
| 38 | Salmeterol (8 mg) | n = 6, m = 6 | 0.1 |
| 39 | Salmeterol (8 mg) | n = 8, m = 4 | 0.1 |
| 40 | Fluticasone Propionate(6mg) | n = 4, m = 10 | 1.0 |
| 41 | Fluticasone Propionate(6mg) | n = 4, m = 4 | 1.0 |
| 42 | Fluticasone Propionate(6mg) | n = 6, m = 6 | 1.0 |
| 43 | Fluticasone Propionate(6mg) | n = 8, m = 4 | 1.0 |

EXAMPLES 44 to 51

Examples 44 to 51 were prepared as described for Examples 32 to 43 but using 1,1,1,2-tetrafluoroethane (P134a) containing 600 ppm of water. Wet propellant was made by mixing water and the propellant in a cylinder, and then shaking over night.

| Example | Drug (amount) | Surfactant type | Surfactant mg/inhaler |
|---|---|---|---|
| 44 | BDP hydrate (12 mg) | n = 4, m = 10 | 1.0 |
| 45 | BDP hydrate (12 mg) | n = 4, m = 4 | 1.0 |
| 46 | BDP hydrate (12 mg) | n = 6, m = 6 | 1.0 |
| 47 | BDP hydrate (12 mg) | n = 8, m = 4 | 1.0 |
| 48 | Salbutamol Sulphate (29 mg) | n = 4, m = 10 | 1.0 |
| 49 | Salbutamol Sulphate (29 mg) | n = 4, m = 4 | 1.0 |
| 50 | Salbutamol Sulphate (29 mg) | n = 6, m = 6 | 1.0 |
| 51 | Salbutamol Sulphate (29 mg) | n = 8, m = 4 | 1.0 |

In the Examples 32 to 51, a range of drug/surfactant ratios (0.2% to 15%) was tested for each compound and each drug. The suspension stability was examined using a back light scattering technique. The suspension stability can be improved at surfactant concentration as low as 0.2% of drug weight. Drug deposition on the walls of the glass vials was also examined and reduced with increases in surfactant concentration. Drug/surfactant ratio as low as 0.1% was able to reduce drug deposition on the glass wall significantly, even at high water content in propellant, demonstrated in Examples 44 to 50.

EXAMPLES 52 to 67

Examples 52 to 67 were prepared as described for Examples 32 to 43 but using aluminium canisters rather than glass vials and 18.2 g 1,1,1,2-tetrafluoroethane (P134a). In Examples 64 to 67 wet P134a containing 350 ppm of water (prepared as described in Examples 44 to 51) was used.

| Example | Drug (amount) | Surfactant type | Surfactant mg/inhaler |
|---|---|---|---|
| 52 | Salbutamol Sulphate (29 mg) | n = 4, m = 10 | 1.0 |
| 53 | Salbutamol Sulphate (29 mg) | n = 4, m = 4 | 1.0 |
| 54 | Salbutamol Sulphate (29 mg) | n = 6, m = 6 | 1.0 |
| 55 | Salbutamol Sulphate (29 mg) | n = 8, m = 64 | 1.0 |
| 56 | Salmeterol (8 mg) | n = 4, m = 10 | 1.0 |
| 57 | Salmeterol (8 mg) | n = 4, m = 4 | 1.0 |
| 58 | Salmeterol (8 mg) | n = 6, m = 6 | 1.0 |
| 59 | Salmeterol (8 mg) | n = 8, m = 4 | 1.0 |
| 60 | Fluticasone Propionate(6mg) | n = 4, m = 10 | 1.0 |
| 61 | Fluticasone Propionate(6mg) | n = 4, m = 4 | 1.0 |
| 62 | Fluticasone Propionate(6mg) | n = 6, m = 6 | 1.0 |
| 63 | Fluticasone Propionate(6mg) | n = 8, m = 4 | 1.0 |
| 64 | BDP hydrate (12 mg) | n = 4, m = 10 | 1.0 |
| 65 | BDP hydrate (12 mg) | n = 4, m = 4 | 1.0 |
| 66 | BDP hydrate (12 mg) | n = 8, m = 4 | 1.0 |
| 67 | BDP hydrate (12 mg) | n = 6, m = 6 | 1.0 |

EXAMPLES 68 to 73

Examples 68 to 73 were prepared as described for Examples 21 to 31, the surfactant employed in each Example 68 to 73 being n=4, m=10.

| Example 68 | Surfactant (amount) | Propellant (amount) |
|---|---|---|
| Salmeterol xinafoate (14mg) | n = 4, m = 10 (3.9mg) | P134a (18.05mg) |

| Example 69 | Surfactant (amount | Propellant (amount) |
|---|---|---|
| Amiloride HCl (32.3mg) | n = 4, m = 10 (1.7mg) | P134a (18.0mg) |

| Example 70 | | |
|---|---|---|
| Salmeterol xinafoate (9.9mg) | n = 4, m = 10 (2.2mg) | P227 (20.8mg) |

| Example 71 | | |
|---|---|---|
| Fluticasone propionate (26.7mg) | n = 4, m = 10 (3.0mg) | P227 (20.7mg) |

| Example 72 | |
|---|---|
| Beclomethasone dipropionate   n = 4, m = 10 (2.2mg)  P227 (20.7mg) (26.9mg) | |

| Example 73 | |
|---|---|
| Amiloride HCl (30.7mg)   n = 4, m = 10 (2.0mg)     P227 (20.7mg) | |

We claim:

1. A pharmaceutical aerosol formulation which comprises particulate medicament, a fluorocarbon or hydrogen-containing chlorofluorocarbon propellant and a surfactant, which is soluble in said propellant, of general formula (Ia) or (Ib)

$$\begin{array}{c} R^1-CH_2 \\ | \\ (R_2-CH)_r \quad O \\ | \quad\quad || \\ CH_2-O-P-X \\ | \\ Y \end{array} \quad (Ia)$$

or $$\begin{array}{c} R^1-CH_2 \quad O \\ | \quad\quad\quad || \\ CH-O-P-X \\ | \quad\quad | \\ R^2-CH_2 \quad Y \end{array} \quad (Ib)$$

wherein:

$R^1$ represents:

$R_F(CH_2)_a$—(CH=CH)$_b$—(CH$_2$)$_c$—(CH=CH)$_d$—(CH$_2$)$_e$—A—;

$R_F$—(CH$_2$)$_f$—OCH$_2$CH(CH$_2$OH)CH$_2$—A—;

$R_F$—(CH$_2$)$_g$—OCH$_2$CH(CH$_2$OH)—A—;

wherein —A— represents —O—, —C(O)O—, —R$^6$(R$^7$)N$^+$—, (wherein each of R$^6$ and R$^7$ represents $C_1$–$C_4$ alkyl or hydroxyethyl), —(CH$_2$)$_t$—, wherein t=0 or 1 or —C(O)N(R$^9$)—(CH$_2$)$_q$—B, wherein q is an integer from 0 to 12, B represents —O— or —C(O)—, and R$^9$ is hydrogen or R$^6$, and wherein the sum of a+c+e is from 0 to 17, the sum b+d is from 0 to 12 and each of f and g is from 1 to 12;

$R_F$—(CH$_2$—CH$_2$—O)$_h$—;

$R_F$—(CH(CH$_3$)CH$_2$O)$_h$—;

$R_F$—(—CH$_2$—CH$_2$—S)$_h$—, wherein h is from 1 to 12; and wherein $R_F$ represents a fluorine-containing moiety having one of the following structures:

(a) F(CF$_2$)$_i$—, wherein i is from 1 to 18, (b) (CF$_3$)$_2$CF(CF$_2$)$_j$—, wherein j is from 0 to 8, (c) $R_F$1(CF$_2$CF(CF$_3$))$_k$—, wherein k is from 1 to 4, and $R_F$1 represents CF$_3$—, C$_2$F$_5$— or (CF$_3$)$_2$CF—, (d) $R_F$2($R_F$3)CFO(CF$_2$CF$_2$)$_l$ wherein l is from 1 to 6 and wherein each of $R_F$2 and $R_F$3 independently represents CF$_3$—, C$_2$F$_5$—, n-C$_3$F$_7$— or CF$_3$CF$_2$CF(CF$_3$)— or $R_F$2 and $R_F$3 taken together represent —(CF$_2$)$_4$— or —(CF$_2$)$_5$—, or (e) one of the structures (a) to (d) in which one or more of the fluorine atoms are replaced by one or more hydrogen or bromine atoms and/or at least two chlorine atoms in a proportion such that at least 50% of the atoms bonded to the carbon skeleton of $R_F$ are fluorine atoms, and wherein $R_F$ contains at least 4 fluorine atoms, r is 0 or 1;

$R^2$ represents $R^1$, hydrogen or a group OR, wherein R represents a saturated or unsaturated $C_1$–$C_{20}$ alkyl or $C_3$–$C_{20}$ acyl;

and when r is 1, $R^1$ and $R^2$ may exchange their positions; and each of X and Y independently represent:

hydroxyl;

—OCH$_2$CH(OH)CH$_2$OH;

—O(CH$_2$CH$_2$O)$_t$R$^3$, wherein t is an integer from 1 to 5; and R$^3$ represents a hydrogen atom or $C_1$–$C_4$ alkyl group;

—NR$^4$R$^5$ or N$^+$R$^4$R$^5$R$^8$, wherein each of R$^4$, R$^5$ and R$^8$ independently represents a hydrogen atom; a $C_1$–$C_4$ alkyl group, —CH$_2$CH$_2$O(CH$_2$CH$_2$O)$_s$R$^3$, wherein s represents an integer of from 1 to 5, or R$^4$ and R$^5$ when taken together represent —(CH$_2$)$_q$ wherein q is an integer of from 2 to 5, or with the nitrogen atom R$^4$ and R$^5$ form a morpholino group;

—O(CH$_2$)$_p$Z wherein Z represents a 2-aminoacetic acid group, —NR$^4$R$^5$ or —N$^+$R$^4$R$^5$R$^8$ where R$^8$ is as defined for R$^4$ and R$^5$ above, and p is an integer of from 1 to 5;

with the proviso that X and Y do not both represent hydroxyl or an ionized form derived from hydroxyl.

2. A pharmaceutical aerosol formulation which comprises particulate medicament, a fluorocarbon or hydrogen-containing chlorofluorocarbon propellant and a surfactant, which is soluble in said propellant, of general formula (I)

$$\begin{array}{c} \quad\quad\quad\quad\quad\quad O \\ \quad\quad\quad\quad\quad\quad || \\ C_nF_{2n+1}(CH_2)_m-C-O-CH_2 \\ \quad\quad\quad\quad\quad\quad\quad\quad\quad | \\ \quad\quad\quad\quad\quad\quad O \quad | \\ \quad\quad\quad\quad\quad\quad || \quad | \\ C_nF_{2n+1}(CH_2)_m-C-O-CH \quad\quad O \quad\quad R^1 \\ \quad\quad\quad\quad\quad\quad\quad\quad\quad | \quad\quad || \quad\quad | \\ \quad\quad\quad\quad\quad\quad\quad\quad\quad CH_2-O-P^\ominus-O-CH_2CH_2N^\oplus-R^2 \\ \quad\quad\quad\quad\quad\quad\quad\quad\quad\quad\quad\quad\quad || \quad\quad\quad\quad\quad | \\ \quad\quad\quad\quad\quad\quad\quad\quad\quad\quad\quad\quad\quad O \quad\quad\quad\quad\quad R^3 \end{array} \quad (I)$$

wherein n is an integer of 1 to 18;

m is an integer of 0 to 17; and $R^1$, $R^2$ and $R^3$ are each independently a hydrogen atom or a $C_{1-4}$alkyl group.

3. A formulation according to claim 2, wherein $R^1$, $R^2$ and $R^3$ each represent methyl.

4. A formulation according to claim 2, wherein n is an integer of 4 to 8.

5. A formulation according to claim 4, wherein n is 4 or 6.

6. A formulation according to any of claim 2, wherein m is an integer of 4 to 10.

7. A formulation according to claim 6, wherein m is 4, 6 or 10.

8. A formulation according to claim 1, wherein the surfactant is present in an amount of 0.05 to 15% w/w, relative to medicament.

9. A formulation according to claim 8, wherein the surfactant is present in an amount of 0.5 to 10% w/w, relative to medicament.

10. A formulation according to claim 1, wherein the particulate size of medicament is in the range of 1–10 microns.

11. A formulation according to claim 1, wherein medicament is present in an amount of 0.01–1.0% w/w, relative to the total weight of the formulation.

12. A formulation according to claim 1, wherein particulate medicament is selected from the group consisting of cromoglycate, salbutamol, salmeterol, terbutaline, reproterol, a beclomethasone ester, a fluticasone ester and (−)-4-amino-3,5-dichloro-α-[[[6-[2-(2-pyridinyl)ethoxy]hexyl]amino]methyl]benzenemethanol.

13. A formulation according to claim 12, wherein particulate medicament is selected from the group consisting of salmeterol xinafoate, salbutamol, fluticasone propionate, beclomethasone dipropionate and physiologically acceptable salts and solvates thereof.

14. A formulation according to claim 2, which comprises (a) an effective amount of a particulate bronchodilatory medicament, (b) an effective amount of a particulate antiinflammatory, (c) a fluorocarbon or hydrogen-containing chlorofluorocarbon propellant, and (d) a surfactant of general formula (I).

15. A formulation according to claim 1, wherein said propellant is $C_{1-4}$ hydrogen-containing fluorocarbon.

16. A formulation according to claim 15, wherein said propellant is selected from 1,1,1,2-tetrafluoroethane ($CF_3CH_2F$) and 1,1,1,2,3,3,3-heptafluoro-n-propane ($CF_3CHFCF_3$).

17. A formulation according to claim 2, which consists essentially of one or more particulate medicament, one or more fluorocarbon or hydrogen-containing chlorofluorocarbon propellant and a surfactant of formula (I).

18. A method of treating respiratory disorders in a human patient, which comprises administration by inhalation of an effective amount of a formulation according to claim 1.

19. A process of preparing a formulation according to claim 1, which comprises dispersal of said medicament and surfactant in said propellant.

* * * * *